United States Patent [19]
Jönsson et al.

[11] Patent Number: 6,149,294
[45] Date of Patent: Nov. 21, 2000

[54] SYSTEM FOR THE PREPARATION OF A FLUID CONCENTRATE INTENDED FOR MEDICAL USE

[75] Inventors: Lennart Jönsson, Furulund; Stefan Knutsson, Bjärred, both of Sweden

[73] Assignee: Gambro AB, Sweden

[21] Appl. No.: 08/982,167

[22] Filed: Dec. 1, 1997

Related U.S. Application Data

[60] Continuation of application No. 08/586,067, Jan. 16, 1996, abandoned, which is a division of application No. 08/261,721, Jun. 17, 1994, Pat. No. 5,511,875, which is a continuation-in-part of application No. 08/003,844, Jan. 11, 1993, Pat. No. 5,344,231, which is a continuation of application No. 07/643,468, Jan. 22, 1991, abandoned.

[30] Foreign Application Priority Data

Feb. 19, 1990 [SE] Sweden .............................. 90 00586-9

[51] Int. Cl.[7] .............................. B01F 15/02; G05D 11/13
[52] U.S. Cl. ........................................ 366/136; 366/152.4
[58] Field of Search ..................................... 366/131, 132, 366/134, 136, 137, 152.4, 153.1, 159.1, 182.1, 182.2, 177.1, 179.1, 341; 222/132, 145.1, 145.5; 137/5, 88, 255, 256, 257, 258; 422/261, 281, 285

[56] References Cited

U.S. PATENT DOCUMENTS

| | | |
|---|---|---|
| 607,562 | 7/1898 | Almstead . |
| 2,701,236 | 2/1955 | Schernekau . |
| 2,890,643 | 6/1959 | King .......................................... 99/291 |
| 3,872,781 | 3/1975 | Hebling ..................................... 99/291 |
| 4,757,754 | 7/1988 | Welker ...................................... 99/291 |
| 5,344,231 | 9/1994 | Jonsson et al. .......................... 366/137 |
| 5,348,389 | 9/1994 | Jonsson et al. .......................... 366/136 |
| 5,460,446 | 10/1995 | Chevallet et al. ....................... 366/136 |
| 5,511,875 | 4/1996 | Jonsson et al. .......................... 366/136 |

*Primary Examiner*—Tony G. Soohoo
*Attorney, Agent, or Firm*—Lerner, David, Littenburg, Krumholz, & Mentlik, LLP

[57] ABSTRACT

Apparatus for the preparation of fluids intended for medical use is disclosed, including a water source and at least one cartridge or other vessel containing a solid such as a powder which is to be dissolved in the water for preparation of the desired fluid. The apparatus includes a container such that the water and a powder can be mixed and a concentrate provided in the container, and a recirculation circuit for recirculation of the water or concentrate solution into the container for further mixing of the water and powder to prepare a concentrate having a predetermined concentration.

39 Claims, 10 Drawing Sheets

SYSTEM FOR THE PREPARATION OF A FLUID CONCENTRATE INTENDED FOR MEDICAL USE

This is a continuation of prior application Ser. No. 08/586,067, filed on Jan. 16, 1996, now abandoned which is a divisional of application Ser. No. 08/261,721, filed on Jun. 17, 1994, now U.S. Pat. No. 5,511,875 which is a continuation-in-part of application Ser. No. 08/003,844, filed Jan. 11, 1993 (now U.S. Pat. No. 5,344,231), which is a continuation of application Ser. No. 07/643,468, filed Jan. 22, 1991 (now abandoned).

FIELD OF THE INVENTION

The present invention relates to systems for the preparation of fluids and fluid concentrates which are intended for medical use. More particularly, the present invention relates to systems for the preparation of concentrate solutions intended for medical uses, such as dialysis fluid, replacement fluids for hemofiltration, and concentrates for the preparation of such fluids. More particularly, the present invention relates to such systems which include a source of pure water and at least one cartridge or other such vessel containing a powder or powder concentrate which is intended to be dissolved in the water for the preparation of the desired fluid.

BACKGROUND OF THE INVENTION

Previous systems for the preparation of such fluids normally operate beginning with one or more liquid based concentrates. For example, U.S. Pat. No. 4,158,034 describes how a concentrate in liquid form is mixed with water for the preparation of a dialysis fluid. In European Patent No. EP-B1-0 22 922, and in U.S. Pat. No. 4,783,273, there is a description of how two liquid-based concentrates can be mixed with water to obtain a fluid intended for medical use, such as a a dialysis fluid. More recently, systems have been introduced which instead make use of one or more concentrates in powder form. For example, U.S. Pat. No. 4,784,495 describes how one or more such powder-based concentrates can be used, with or without the addition of a liquid-based concentrate.

Should one wish to utilize a powder-based concentrate which is difficult to dissolve, it can become quite difficult to achieve acceptably rapid dissolution such as by using the system disclosed in the above-mentioned U.S. Pat. No. 4,784,495. Furthermore, the system according to this patent can become relatively complicated if it is desired to add several different individual pre-packed powder-based concentrates.

SUMMARY OF THE INVENTION

In accordance with the present invention, these are the problems that have now been solved by the discovery of apparatus for the preparation of a concentrate solution from water and powder or powder concentrate comprising water supply means for supplying water, mixing means comprising a container whereby the water supply means can supply the water to the container and the powder or powder concentrate can be mixed with the water in the container to provide the concentrate solution, withdrawal means for withdrawing the concentrate solution from the container, and recirculation means for recirculating the concentrate solution into the container for further mixing of the water with the powder or powder concentrate to further concentrate the concentrate solution to a predetermined concentrate. In accordance with this invention, this apparatus can thus be used for the preparation of fluids intended for medical use, such as dialysis fluid, replacement fluid for hemofiltration, or a concentrate for the preparation of such fluids.

In accordance with a preferred embodiment of the apparatus of the present invention, the recirculation means thus includes cartridge means whereby during recirculation the water or concentrate solution passes through the cartridge means so that powder or powder concentrate contained within the cartridge means can be mixed with the water or the recirculating concentrate solution to provide the concentrate solution and to further concentrate the concentration solution.

In accordance with the present invention, a system is thus provided which includes means for conducting water to a mixing vessel and which includes a recirculation circuit which includes the mixing vessel as well as one or more cartridges or means for connecting one or more cartridges thereto, and means for recirculation of the water or partially prepared concentrate solution through one or more of the cartridges until an appropriate concentration is obtained by dissolving the powder either partially or fully into the solution. By use of such a recirculation circuit, even relatively difficult to dissolve powder-based concentrates can now be dissolved appropriately, and at the same time liquid-based concentrates can be prepared in the mixing vessel from one or more powder-based concentrates which, after preparation, can be conveyed to conventional dialysis machines which would otherwise normally receive such liquid-based concentrates from one or more containers therefor.

In accordance with a preferred embodiment of the apparatus of the present invention, the recirculation means includes a plurality of cartridge members and flow control means for controlling the flow of the recirculation means whereby the water or concentrate solution circulating in the recirculation means can be selectively directed to one of the plurality of cartridge members to mix powder or powder concentrate contained within that one of the cartridge members with the water or concentrate solution. These plurality of cartridges are thus connected in parallel for such selective connection to the recirculation circuit. In this manner, the precise desired amount of concentrate for the patient can be removed from each cartridge; i.e., an individual dosage can be obtained therefrom.

Furthermore, since not all substances are suitable for use in a powdered form, one or more of the cartridges connected in such a parallel arrangement can constitute a vessel for a liquid-based concentrate which is intended to be included in the finally prepared concentrate fluid therefor.

In accordance with a preferred embodiment of the apparatus of the present invention, the pump means comprises a metering pump for metering the water or concentrate solution provided by the mixing means.

In accordance with another embodiment of the apparatus of the present invention, the recirculation means includes conductivity measuring means for measuring the conductivity of the concentrate solution, whereby the recirculation of the concentrate solution in the recirculation means can be controlled thereby. In this manner, the recirculation through the particular cartridge can be terminated when the desired conductivity is obtained. Suitable such means for measuring the concentration, such as pH meters or ion-selective meters, can also be used for this purpose. Indeed, when conductivity meters are referred to throughout this specification, this same type of substitution can be made therefor.

In accordance with a preferred embodiment of the apparatus of the present invention, when a plurality of cartridges in parallel are employed in the recirculation means, the flow through these cartridges can be controlled by a valve unit, which is arranged to selectively connect the cartridge and/or vessel to the recirculation circuit.

In accordance with another embodiment of the apparatus of the present invention, there is also provided secondary cartridge means, and the water supply means includes secondary water conduit means for conducting the water to the secondary water cartridge means, whereby additional powder or powder concentrate contained within the secondary cartridge means can be mixed with the water and a secondary concentrate solution produced therein, and secondary mixing means for mixing the secondary concentrate solution with the concentrate solution withdrawn from the recirculation means by the withdrawal means so as to provide a combined concentrate solution. In this manner, not all of the cartridges need to be included in the recirculation circuit and, instead, the water can be also conducted directly to a cartridge which is connected in parallel to the other cartridges for dissolving the substance therein which is intended to form part of the finally prepared concentrate solution.

In a preferred embodiment, a conductivity measuring means for measuring the conductivity of the secondary concentrate solution is provided, or conductivity measuring means for measuring the conductivity of the combined concentrate solution, or conductivity measuring means for measuring both conductivities. Furthermore, if such conductivity measurements are made both before and after mixture of these two solutions, then a differential conductivity means may be utilized. This is particularly suitable where only a small change in conductivity occurs due to the mixing of these two solutions.

In accordance with another embodiment of the apparatus of the present invention, in the case where conductivity measuring means for measuring the conductivity of the combined concentration solution is employed, the recirculation means preferably includes metering pump means for controlling the flow of the combined concentrate solution. The use of an accurate metering dosage pump theoretically permits one to calculate which portion of the conductivity is due to the concentrate solution and which portion is due to the dissolved concentrate in the secondary concentrate solution.

In accordance with another embodiment of the apparatus of the present invention, closure valve means are provided in connection with the water supply means, whereby the supply of water can be terminated when the mixing means contains a predetermined quantity of water. The mixing vessel can, for example, include a level indicator which, in turn, controls the closure valve means arranged in the water supply means.

In accordance with another embodiment of the apparatus of the present invention, cartridge means are associated with the water supply means whereby powder or powder concentrate contained within the cartridge means can be mixed with the water and supplied to the mixing means therefrom. This embodiment is particularly useful when liquid-based or very readily dissolvable powder concentrates are to be supplied to the mixing means.

In accordance with this invention, the cartridges and/or vessels discussed above can initially contain an excess of powder concentrate, such that circulation in the recirculation circuit can be interrupted before the cartridge or other vessel connected to the recirculation circuit is totally empty. In this manner, it is assured that the desired concentration of the added substance can always be obtained.

In accordance with a preferred embodiment of the apparatus of the present invention, the apparatus includes tertiary cartridge means and the water supply means includes tertiary water conduit means for conducting the water to the tertiary cartridge means, whereby additional powder or powder concentrate contained within the tertiary cartridge means can be mixed with the water and a tertiary concentrate solution produced therein, and tertiary mixing means for mixing the tertiary concentrate solution with at least one of the concentrate solutions drawn from the recirculation means by said withdrawal means and said secondary concentrate solution. Preferably, the apparatus also includes conductivity measuring means for measuring the conductivity of the tertiary concentrate solution, and/or conductivity measuring means for measuring the conductivity of the one of the combined concentrate solutions and the secondary concentrate solution.

In accordance with one embodiment of the apparatus of the present invention, the mixing means comprises a cartridge or other vessel which contains the desired quantity of a salt from the outset. In this manner, this salt can also be readily dissolved in the recirculation circuit thereof, and when fully dissolved this can be checked by means of a conductivity meter, for example. Particular advantages can also be obtained if the mixing vessel contains a small quantity of liquid, preferably water, in addition to that salt in a manner such that a concentrated liquid or mud of that liquid and the powder-based salt is formed therein. Such a concentrated liquid can be more readily checked to see that it is lump-free compared with a generally compacted powder in dry form.

In accordance with another embodiment of the apparatus of the present invention, heating means are included in the recirculation means for heating the concentrate solutions recirculating in the recirculation means. This permits the salt in the form of a dry powder or concentrated liquid to be more readily dissolved.

In accordance with another embodiment of the apparatus of the present invention, the apparatus includes acid supply means for supplying acid to the recirculation means. Preferably, the acid supply means includes acid storage means for storing the acid and acid pump means for pumping the acid from the acid storage means to the recirculation means. This embodiment particularly applies to the case where the mixing vessel contains a concentrated liquid aside from the salt. Many medical solutions, such as dialysis fluids, should actually contain such an acid, and in this case it can be added before preparation of the final solution. As an alternative, the acid can be added by means of the recirculation circuit being connected to a branch circuit with a dosage pump arranged to pump an acid in liquid form from a storage vessel to the recirculation circuit.

In accordance with another embodiment of the apparatus of the present invention, the recirculation means includes sterile filter means for filtering the concentrate solution before the concentrate solution enters the mixing means.

In accordance with another embodiment of the apparatus of the present invention, the recirculation means includes quick release connection means connecting the mixing means to the recirculation means, whereby the mixing means can be readily uncoupled from the recirculation means. In this manner, the mixing vessel can then be easily coupled to, for example, a dialysis machine instead of the traditionally employed dialysis concentrate container.

In accordance with a preferred embodiment of the apparatus of the present invention, the mixing means comprises a flexible plastic bag. By using such a bag, it can be readily observed whether the salt is lump-free whether it is in dry form or in the form of a liquid concentrate, or in the form of a salt slurry.

DETAILED DESCRIPTION OF THE PREFERRED EMBODIMENTS

Figure 1:
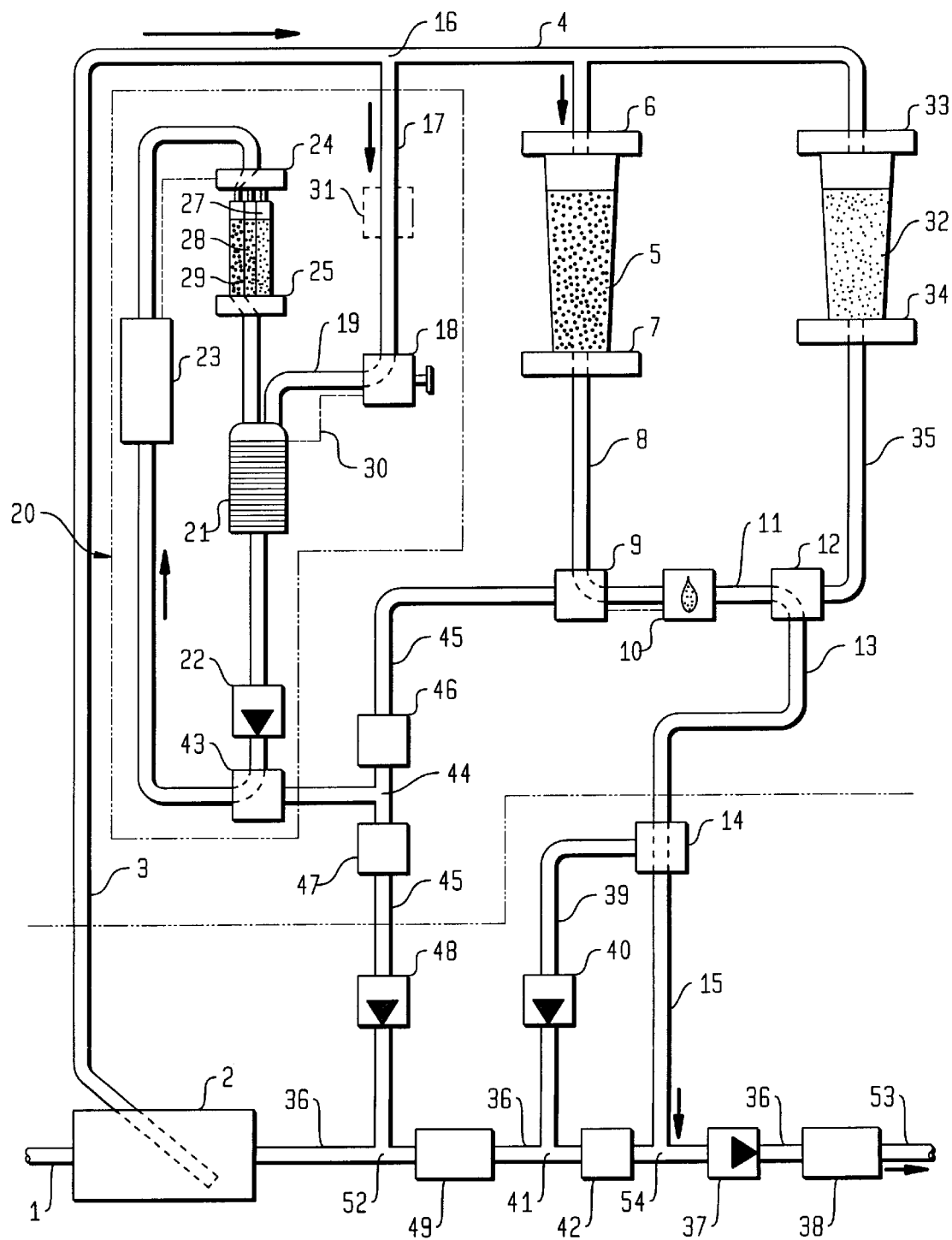
FIG. 1 is a schematic representation of a preferred embodiment of the system in accordance with the present invention.
Figure 2:
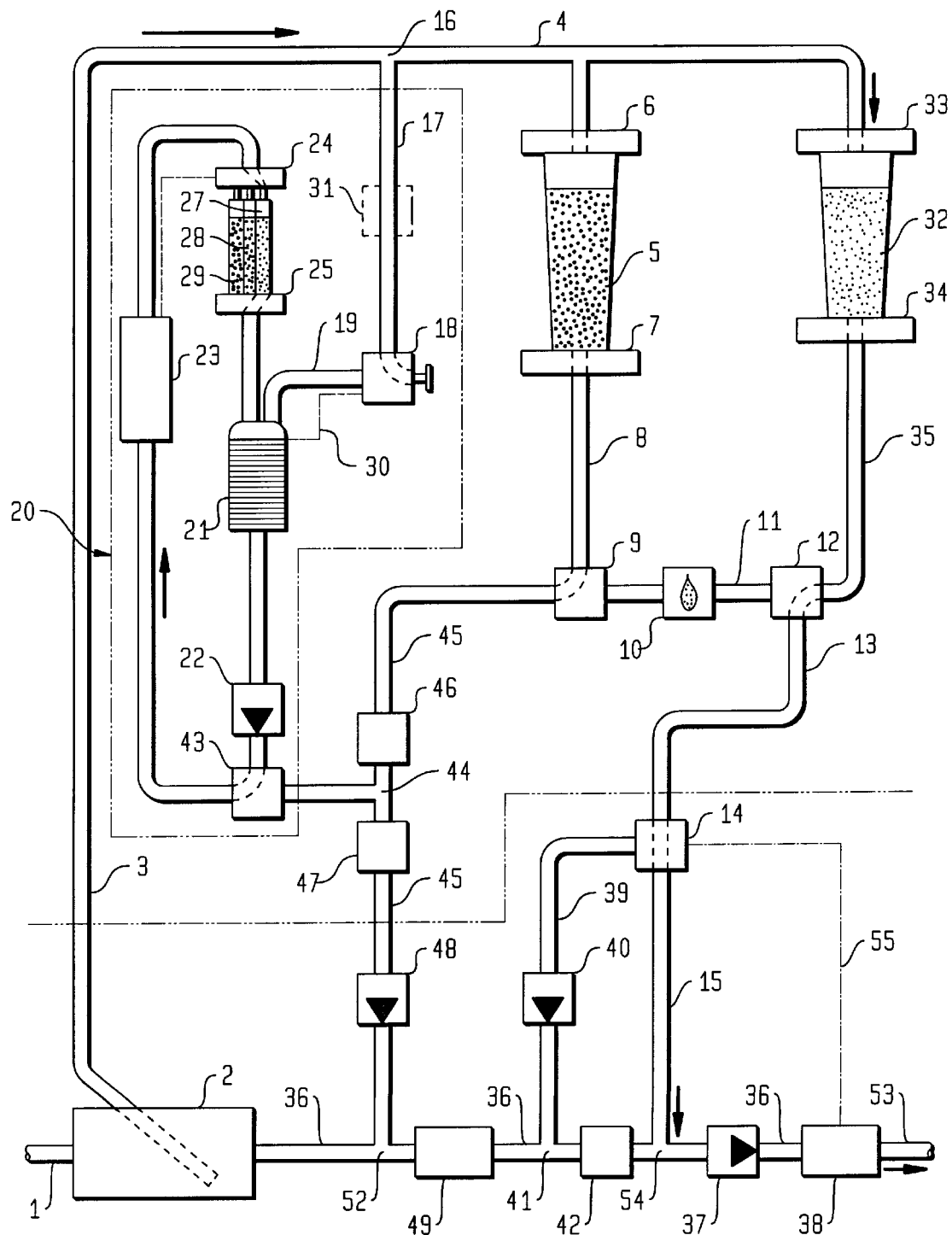
FIG. 2 is a schematic representation of the system shown in FIG. 1 in an altered form.
Figure 3:
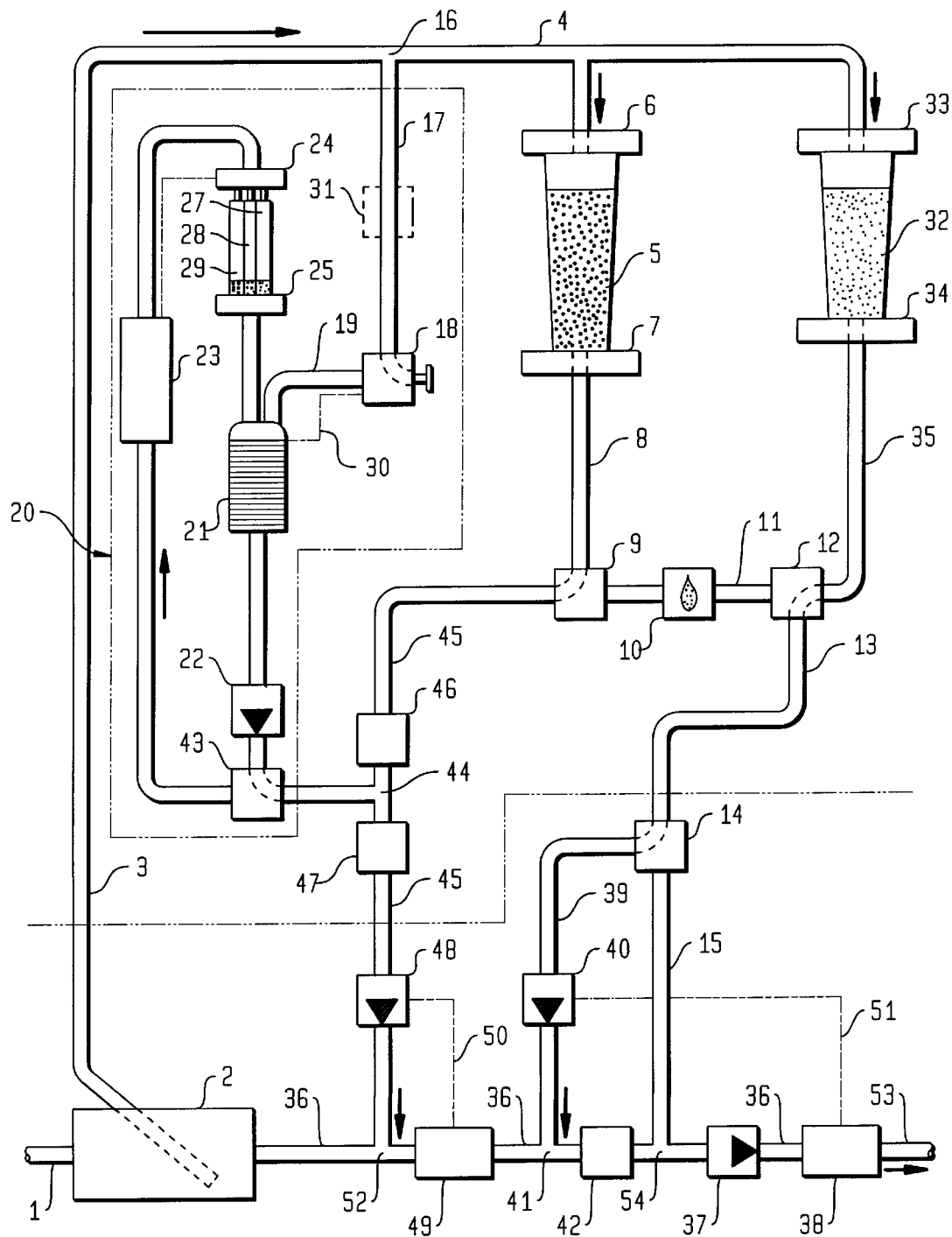
FIG. 3 is a schematic representation of the system shown in FIG. 1 in a further altered form.

Referring to the Figures, in which like reference numerals refer to like portions thereof, FIGS. 1–3 show by way of a block diagram a preferred embodiment of the system according to the present invention in its three different configurations. FIG. 1 is intended to show how a recirculation circuit 20, and a separate powder cartridge 5 are, respectively, filled with water. The water is taken from an inlet 1, through a heating vessel 2, and through conduits 3 and 4 to powder cartridge 5, which is located between two connection pieces 6 and 7. When the cartridge 5 is filled, the water is further passed as shown in FIG. 1 through a conduit 8 and a valve 9 to a detector 10, which detects the water and/or concentrate dissolved therein. It is possible to carry this out with a time delay so that the fluid will have time to fill conduit 11, valve 12, conduit 13, valve 14, and conduit 15.

At the same time, water is conveyed from a branch point 16 through conduit 17, valve 18 and conduit 19, to a recirculation circuit, which in its entirely is denoted by reference numeral 20. Recirculation circuit 20 includes a mixing vessel 21, a recirculation pump 22, a concentration measuring device 23, such as a conductivity meter, and between two valve units 24 and 25, there are connected in parallel a number of cartridges or other vessels 27, 28 and 29 for one or more powder concentrates or liquid-based concentrate. When a sufficient quantity of fluid has been supplied to the mixing vessel 21, valve 18 is closed. This can occur with the assistance of a level indicator, which is schematically shown in FIG. 1 by the dashed line 30. Thereafter, the recirculation pump 22 is initiated, along with valve units 24 and 25, which are so positioned that the water is passed through one of the vessels or cartridges 27–29. In FIG. 1 it is vessel 29 which is shown as being thus connected. When the desired conductivity is obtained, which is measured by means of meter 23, the next cartridge 28 can then be connected, and finally cartridge 27. Should the prepared fluid in mixing vessel 21 include another liquid-based or easily dissolvable concentrate, then dissolution can occur during the filling of mixing vessel 21, with the vessel containing this concentrate being connected to conduit 17. Such a vessel 31 is shown in FIG. 1 by means of dashed lines.

When the recirculation circuit 20 is filled, valve 18 is closed, as shown in FIG. 2. In the same manner, valve 9 is actuated when vessel 5 is filled. This valve position is also shown in FIG. 2. At the same time, valve 12 is switched from the position shown in FIG. 1 to that shown in FIG. 2, so that water from conduit 4 can pass to another vessel or powder cartridge 32, which is located between two connection pieces 33 and 34. When cartridge 32 has been filled, the water with dissolved concentrate therein can be conducted through conduit 35, valve 12, conduit 13, valve 14 and conduit 15 to a main line or conduit 36, which includes a pump 37 and a detector 38, such as a conductivity measuring device. Detector 38 controls valve 14, so that it is then switched to the position shown in FIG. 3. The fluid from vessel 32 is now conveyed from valve 14 through a conduit 39, which includes a dosage pump 40, to the main line 36 at a point 41 upstream of a restrictor 42. This restrictor 42, together with pump 37 and a gas trap, arranged further downstream (not shown in FIG. 3), is used for degasing the prepared fluid.

By switching valve 14 to the position shown in FIG. 3, the system is ready to provide a solution for use in dialysis. An inlet valve 43 in the recirculation circuit 20 is thus actuated so the pump 22 can pump prepared fluid from the mixing vessel 21 to a mixing point 44, to which concentrate from the vessel 5 is conducted by means of valve 9 and conduit 45. The appropriate concentration of the dissolved substance is measured in this conduit upstream and downstream of the mixing point 44. This can be achieved, for example, by means of a differential conductivity meter, whose measuring points are denoted by reference numerals 46 and 47, respectively. The prepared solution can then be conducted further through conduit 45 by means of pump 48, which preferably consists of an accurately metering dosage pump. The prepared solution can thus be conducted to the main line 36, in which the concentration is once more checked by means of a meter 49, such as another conductivity measuring device. This meter 49 then controls pump 48, as shown by the dotted line 50 in FIG. 3. Additional concentrate is then added to the prepared solution at mixing point 41 by means of a pump 40, which is controlled by measuring device 38, as indicated by the dotted line 51. By means of measuring device 38, which preferably consists of a conductivity meter, it is possible to regulate the final concentration of the concentrate solution obtained from the system according to this invention.

Figure 4:
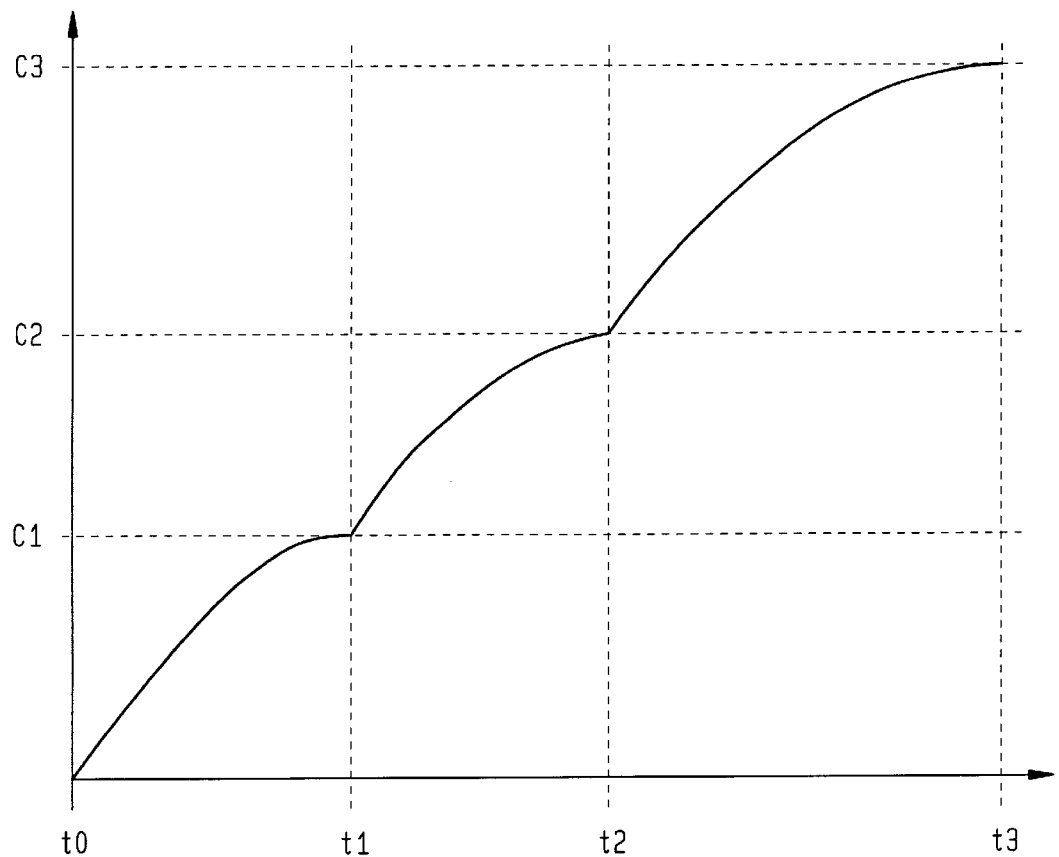
FIG. 4 is a graphical representation measuring conductivity versus time using the supply of three different concentrates in accordance with the system shown in FIGS. 1–3.

Referring next to FIG. 4, there is shown a diagram of how the conductivity varies in recirculation circuit 20. It is assumed in this case that meter 23 consists of a conductivity measuring device, and that vessels 27, 28 and 29 contain three different salts. Thus, between time t0 and t1 one of these vessels is connected, until conductivity value c1 is obtained. Thereafter, the next vessel is connected until conductivity value c2 is reached. Then the third or final vessel is connected until the conductivity obtains the desired value c3. At this point, valve 43 is switched over so that the thus-prepared solution can be conducted to mixing point 44. At this mixing point, concentrate from vessel 5 is added. The mixture thus obtained is then fed to mixing point 52 in main line 36, where it is mixed with water from heating vessel 2. At the next mixing point 41, concentrate from vessel 32 is then added. After a final check in the measuring device 38, the thus-prepared solution can then be conducted to its place of consumption, as symbolized by arrow 53.

Figure 5A:
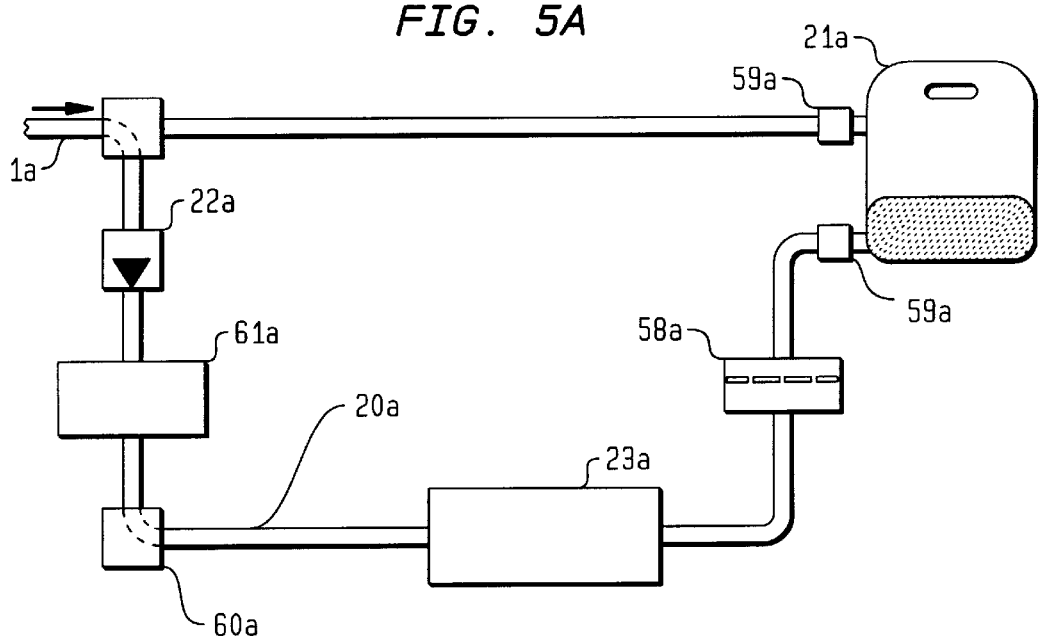
FIG. 5a is a schematic representation of a modified embodiment of the system in accordance with the present invention.
Figure 5B:
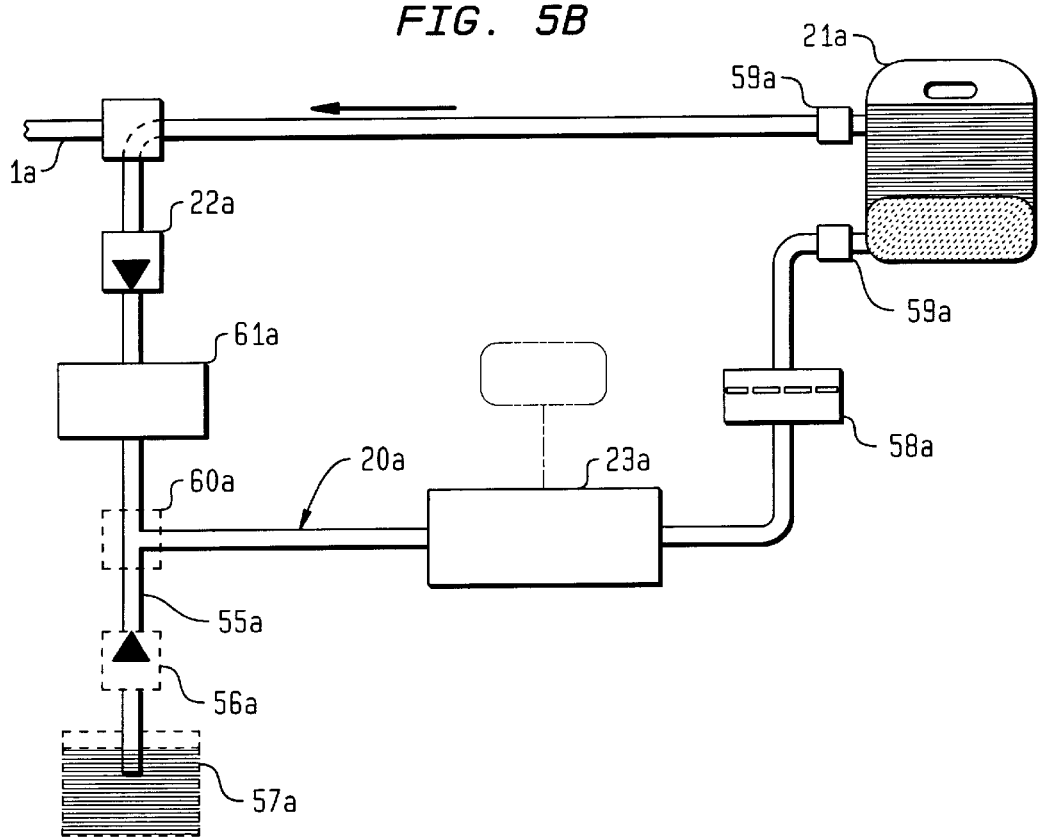
FIG. 5b shown a schematic representation of a further modified embodiment of the system in accordance with the present invention.

Finally, FIGS. 5a and 5b show a modification of the system according to the present invention. Since this modification still corresponds in principal to the above-described system, the same reference numerals have been used, but with the addition of a. In this system, pure water enters through inlet 1a and is pumped by means of pump 22a through recirculation circuit 20a, which includes a heater 61a, a control device, such as a conductivity meter 23a, a sterile filter 58a and a mixing vessel 21a. Utilizing this arrangement, mixing vessel 21a should contain the desired quantity of salt from the outset. This salt can possibly be in a dry form, or it can be a concentrated liquid obtained by adding a small quantity of liquid thereto. Such a concentrated liquid can be complemented by the addition of any necessary acid in liquid form. Such acid may, however, also be added in different forms. Certain acids can, for example, be obtained in the form of a dry powder.

Acid in liquid form can be added through a branch conduit 55a with a dosage pump 56a, as is shown in FIG. 5b. The acid can thus be drawn from a vessel 57a, and introduced into the recirculation circuit by means of valve 60a. The mixing vessel 21a is preferably connected to the recirculation circuit 20a by means of quick-release connectors 59a, so that it can be readily uncoupled and connected, for example, to a dialysis machine, instead of the traditionally employed dialysis concentrate container.

EXAMPLE 1

Utilizing the system described in FIGS. 5a and 5b for preparation of a dialysis liquid solution, the following mixture was present in vessel 21a:

NaCl in an amount of about 1,050 grams
KCl in an amount of about 25 grams
CaCl in an amount of about 45 grams
MgCl in an amount of about 34 grams All of these salts were present in the form of a powder. To this was added approximately 2 dl of fluid, essentially comprising water, but to which approximately 32 g of acetic acid had been added. In this case a flexible plastic bag was used for the mixing vessel 21a. In this manner, it was possible to check that a lump-free concentrated liquid was obtained. It should be appreciated, however, that a somewhat smaller quantity of liquid can be used. Alternatively, an excess of liquid can be added, but for practical reasons it is advisable to keep the weight of the mixing vessel 21a and its contents down.

In the slurry thus obtained, KCl, $CaCl_2$ and $MgCl_2$, are essentially completely dissolved, and NaCl is partly dissolved and partly in the nature of freely movable grains. Such a slurry is easily dissolvable by adding about 5 l of water and recirculating the solution.

EXAMPLE 2

The following mixture was present in vessel 21a:

KCl in an amount of about 15 grams
$CaCl_2$ in an amount of about 45 grams
$MgCl_2$ in an amount of about 18 grams All of these salts were present in powder form. After adding water to about 500 ml of solution, and recirculating the mixture, a concentrate solution was obtained. This concentrate solution should be diluted in a ratio of 1:400 with regard to the final dialysis solution obtained. NaCl and bicarbonate were added to the concentrate solution from powder cartridges 5 and 32, respectively, as shown in FIG. 3.

EXAMPLE 3

The following mixture was present in vessel 21a:

$CaCl_2$ in an amount of about 51 grams
$MgCl_2$ in an amount of about 20 grams.

Both of these salts were present in the form of a powder. After adding water to 500 ml of solution, and subjecting the solution to recirculation, a concentrate solution was obtained. This concentrate solution should be diluted in a ratio of 1:400 with regard to the final dialysis solution obtained. NaCl and bicarbonate was added to the concentrate solution from powder cartridges 5 and 32, respectively, as best shown in FIG. 3.

EXAMPLE 4

The following mixture was present in vessel 21a:

NaCl in an amount of about 1050 grams
KCl in an amount of about 13 grams
CaCl in an amount of about 45 grams
MgCl in an amount of about 18 grams
Glucose in an amount of about 340 grams.

All of the substances were present in the form of a dried powder. When the aforementioned substances were mixed with about 5 l of water, and were subjected to recirculation, a concentrate solution was prepared. This concentration should be diluted during use in a ratio of about 1:34.

The embodiment shown in FIGS. 5a and 5b may be used as a separate apparatus for preparing a dialysis solution. The container 21a may then be disconnected from the apparatus and may subsequently be placed in correspondence with a dialysis preparation machine, at which time the final concentrate solution obtained can be utilized. Alternatively, the embodiment shown in FIGS. 5a and 5b could be used directly as part of a dialysis preparation machine.

Figure 6:
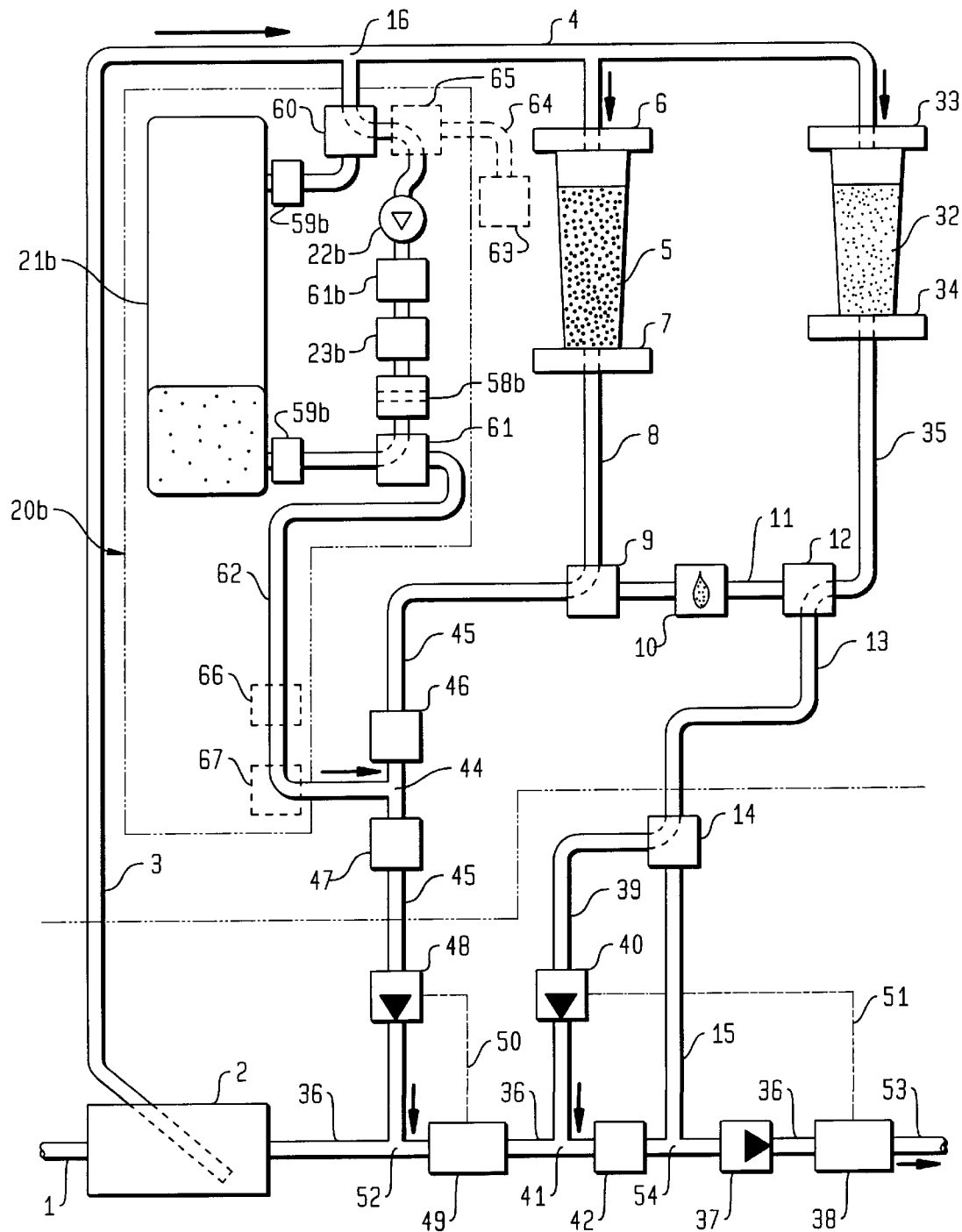
FIG. 6 is a schematic representation of a further modified embodiment of the system in accordance with the present invention.

FIG. 6 discloses a third embodiment of the present invention, wherein the recirculation circuit 20, shown in FIG. 3, is replaced with a recirculation circuit similar to that shown in FIG. 5a. The same reference numerals used in FIG. 5a will be used to represent like components with regard to FIG. 6 with the exception that reference letter "a" will be replaced with reference letter "b". With this in mind, the recirculation circuit 20b of FIG. 6 comprises a plastic bag 21b which may include any of the substances discussed hereinabove with regard to Examples 1–4. The size of the bag 21b is selected so that the interior volume thereof can retain each of the powder substances as well as the water to be added for forming a final concentrate solution.

Optionally, the recirculation circuit 20b may comprise a metering pump 22b to facilitate recirculation of the concentrate solution. A concentration meter 23b may be used to check the concentration of the solution in the recirculation circuit. Preferably, the concentration meter 23b will comprise a conductivity meter, although other suitable concentration detecting meters may be utilized, such as pH meters, temperature detecting meters, ion-selective meters, or the like. A sterile filter 58b may be used in the recirculation circuit 20b to prevent particulate matter, greater than a predetermined size, from entering and/or leaving the bag 21b. Coupling connectors 59b are preferably arranged between the bag 21b and associated conduits within the recirculation circuit. Connectors 59b are preferably quick-release connectors so that the bag 21b may easily be placed into and removed from the recirculation circuit 20b. An inlet valve 60 permits water, or recirculated concentrate solution, to enter and/or leave the bag 21b. An outlet valve 61 is arranged within the recirculation circuit 20b to permit concentrate solution to flow out of the bag 21b when the concentrate solution has reached a predetermined level of concentration. A heater 61b may be arranged within the recirculation circuit 20b to facilitate dissolution of the powdered substances within the bag 21b. It should be appreciated that although a plastic bag 21b is disclosed for use in connection with the apparatus shown in FIG. 6, various other containers, including flexible and rigid containers may be used in additional embodiments.

In operation, the plastic bag 21b is initially filled with the desired amount of solid substances, preferably in powdered form, which are intended to be dissolved. The plastic bag 21b is then connected within the recirculation circuit 20b via quick release connectors 59b. Valve 60 and 61 are adjusted to the position shown in FIG. 6, and the metering pump 22b is utilized to deliver a predetermined quantity of water through valve 61 and into bag 21b through its lower conduit connected thereto via quick release connector 59b. In Example 1, bag 21b will receive about 5 liters of water. In Example 2, bag 21b will receive about 500 ml of water.

After the desired amount of water is introduced into bag 21b, valve 60 is actuated to connect the upper quick release connector 59b to the inlet side of the pump 22b so that the contents of the bag 21b may be recirculated within the recirculation circuit 20b. During recirculation, water, or other desired liquid, and possibly dissolved substances are withdrawn from the upper end of the bag 21b. The withdrawn liquid is then introduced into the lower end of the bag 21b for agitating the powder, or other solid substances, therein in the lower part of the bag 21b.

The conductivity meter 23b is monitored to determine when the recirculating concentrate solution reaches a predetermined conductivity. Depending on the original content of the bag 21b and the amount of water produced therein, the recirculation of the concentrate solution is then terminated and valve 61 is actuated to its second position, which connects the output end of the pump 22b to mixing point 44 via conduit 62. The prepared concentrate solution in bag 21b is then withdrawn from the upper end thereof and is subsequently metered therefrom at a predetermined rate to mixing point 44 via metering pump 22b. Optionally, the delivery rate of the concentrate solution in conduit 62 can be monitored with a monitoring device, such as a flow meter disclosed in Swedish Patent Application 93.02956-9, or the like.

Bag 21b is preferably provided with internal reinforcement means (not shown) which effectively prevents the upper portion thereof from collapsing after concentrate solution is removed therefrom. Thus, the reinforcement means facilitates withdrawal of the entire contents of the bag 21b from the upper connection thereof.

FIG. 6 also illustrates another preferred embodiment of the present invention, wherein the recirculation circuit includes acid supply means for supplying an acid such as acetic acid during dissolution of the powdered substances. In this regard, the acid supply means are shown in FIG. 6 in phantom and may comprise a container 63, a conduit 64 and a valve 65. When this embodiment is utilized, the acid is initially enclosed within the container 63. The conduit 64 is connected between the container 63 and the valve 65 which permits the acid from the container 63 to be introduced into the recirculation circuit. The metering pump 22 may be used to withdraw acid initially retained within container 63 so that the acid may form part of the concentrate solution. When acid is to be added into the recirculation circuit, valve 65 is actuated to a position which permits metering pump 22 to cause a predetermined amount of acid to be removed from the container 63 and into the bag 21b.

In still another embodiment of the present recirculation circuit, monitoring of the conductivity of the concentrate solution to be prepared is performed in a different way than that described hereinabove. In order to best appreciate this additional means of monitoring the conductivity of concentrate solution as it is being prepared, reference should be made to the graphical illustration shown in FIG. 7.

According to this embodiment of the present invention, a predetermined amount of water which is less than the total amount which will ultimately be used to dissolve solid substances, is initially supplied to bag 21b. In one example, the initial predetermined amount of water may be ninety percent (90%) of the total amount to be added. After the initial amount of water is supplied into the bag 21b, operation of the recirculation circuit 20b is performed until the conductivity of concentrate solution being prepared no longer increases. This level of concentration may be achieved when the derivative of the conductivity equals a low value. All of the solid substances, which were previously retained within bag 21b, are completely dissolved at this point.

Figure 7:
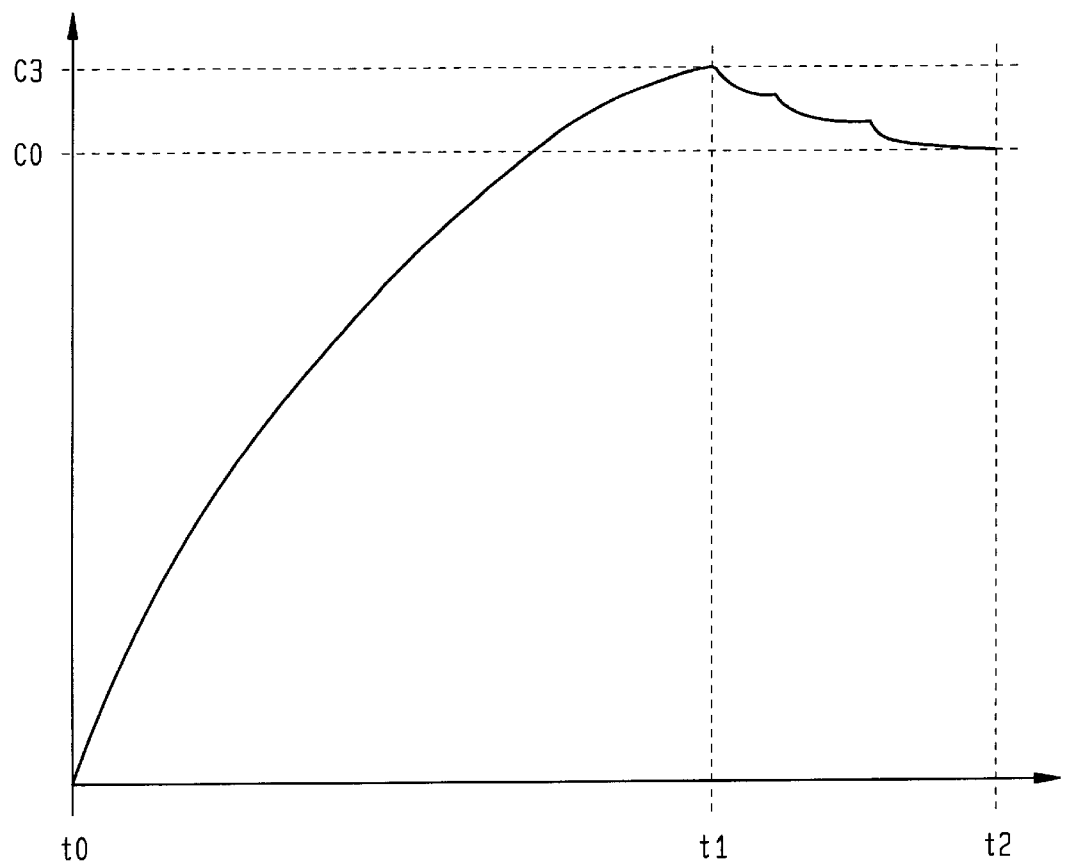
FIG. 7 is a graphical representation measuring conductivity versus time in accordance with one aspect of the present invention.

With reference to FIG. 7, this initial high level of concentration is obtained at time t1, where the concentration level of C3 is obtained. Concentration level C3 is above the desired level of concentration which will be obtained in the final concentrate solution. At this time, valve 60 is actuated to permit the pump 21b to cause an additional amount of water to flow into bag 21b. Recirculation of the concentrate solution then continues until the conductivity of the solution is stabilized at a decreased level. This decreased level is not yet as low as the desired level of conductivity for the final concentrate solution. An additional amount of water is then again introduced into bag 21b to further reduce the concentration level of the concentrate solution. This process is repeated until the concentration level has decreased stepwise, or in a continuous fashion, until the concentrate solution has reached its desired target concentration level C0 at time t2. By obtaining the desired concentration in this manner, it can be assured that the conductivity, and thus the concentration of the solid substances initially retained within bag 21b, are accurately obtained for subsequent use.

In order to obtain the final concentration level in accordance with this embodiment of the present invention, an additional conductivity meter 66 (shown in phantom in FIG. 6) may be used to communicate with conduit 62 to accurately obtain the concentration level of the concentrate solution. Further, if it is desired to use a flow meter, such as flow meter 67 (also shown in phantom), the pump 22b may be a different type of pump, such as a centrifugal pump or a gear-type pump, since the accuracy of a metering pump would not be needed.

Figure 8:
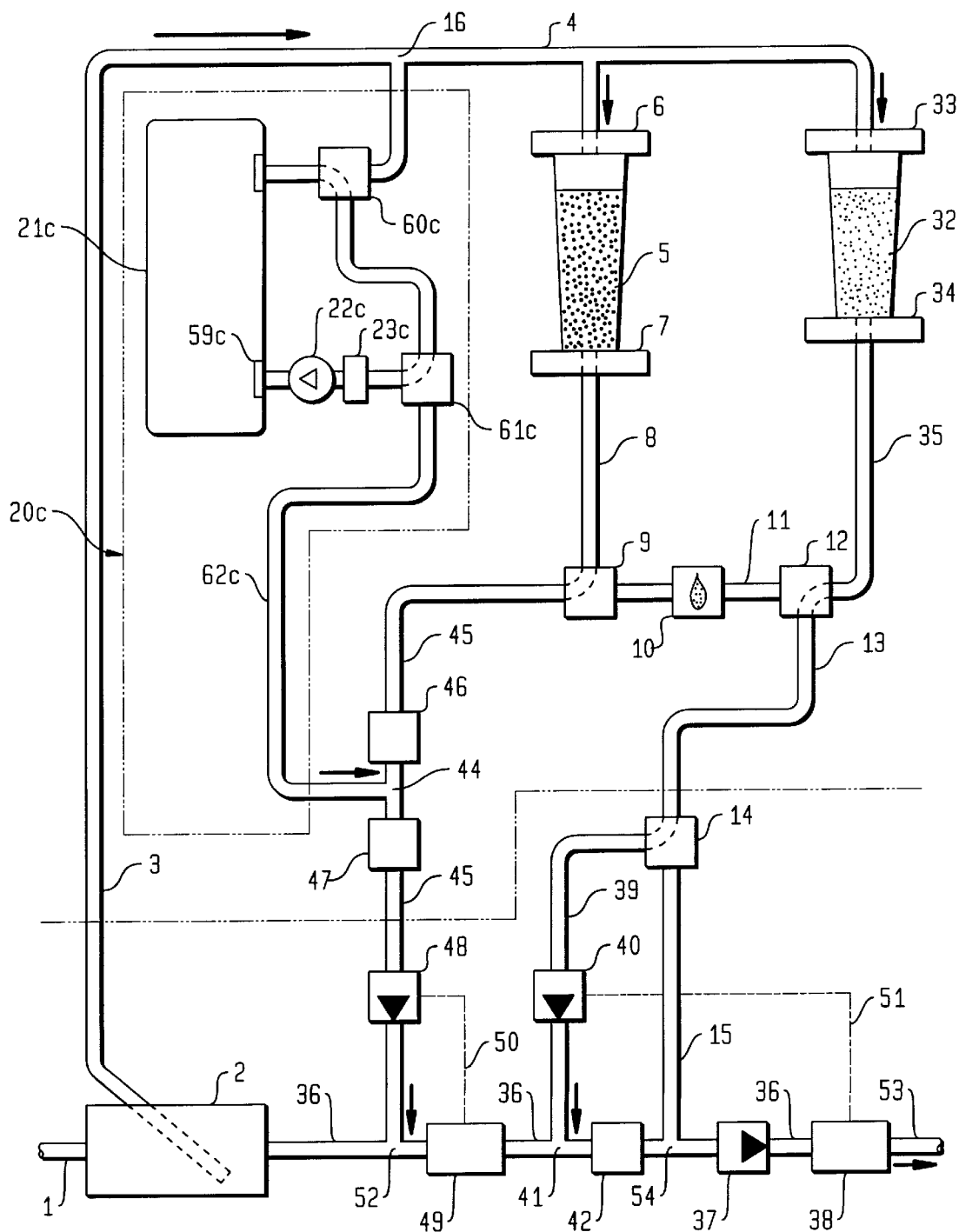
FIG. 8 is a schematic representation of a further modified embodiment of the system in accordance with the present invention.

A further embodiment of the present invention is shown in FIG. 8. This embodiment also includes similar features to the features of the embodiment shown in FIG. 6 so similar reference numerals will be used except that reference letter "b" will be replaced with "c". The difference between the embodiment shown in FIG. 6 and the embodiment shown in FIG. 8 primarily relates to the placement of the pump 22c and the conductivity meter 23c.

In this regard, pump 22c is connected immediately before the lower connector 59c, and the conductivity meter 23c is connected immediately before the pump 22c. The outlet valve 61c is connected immediately before the conductivity meter 23c. The operation of the embodiment shown in FIG. 8 is similar to that shown in FIG. 6 in that water is initially introduced into the bag 21c, and recirculation is subsequently performed as described in connection with FIG. 6. After a final concentrate solution is obtained, outlet valve 61c is actuated into its second position and pump 22c is reversed to withdraw the final concentrate solution from the lower connection 59c. The final concentrate solution is then forced to flow through the conductivity meter 23c and through conduit 62c to the mixing point 44. Since the lower connection 59c is used to withdraw the final concentrate solution from the bag 21c, it is not essential to utilize upper reinforcement means within the bag in this embodiment.

Figure 9:
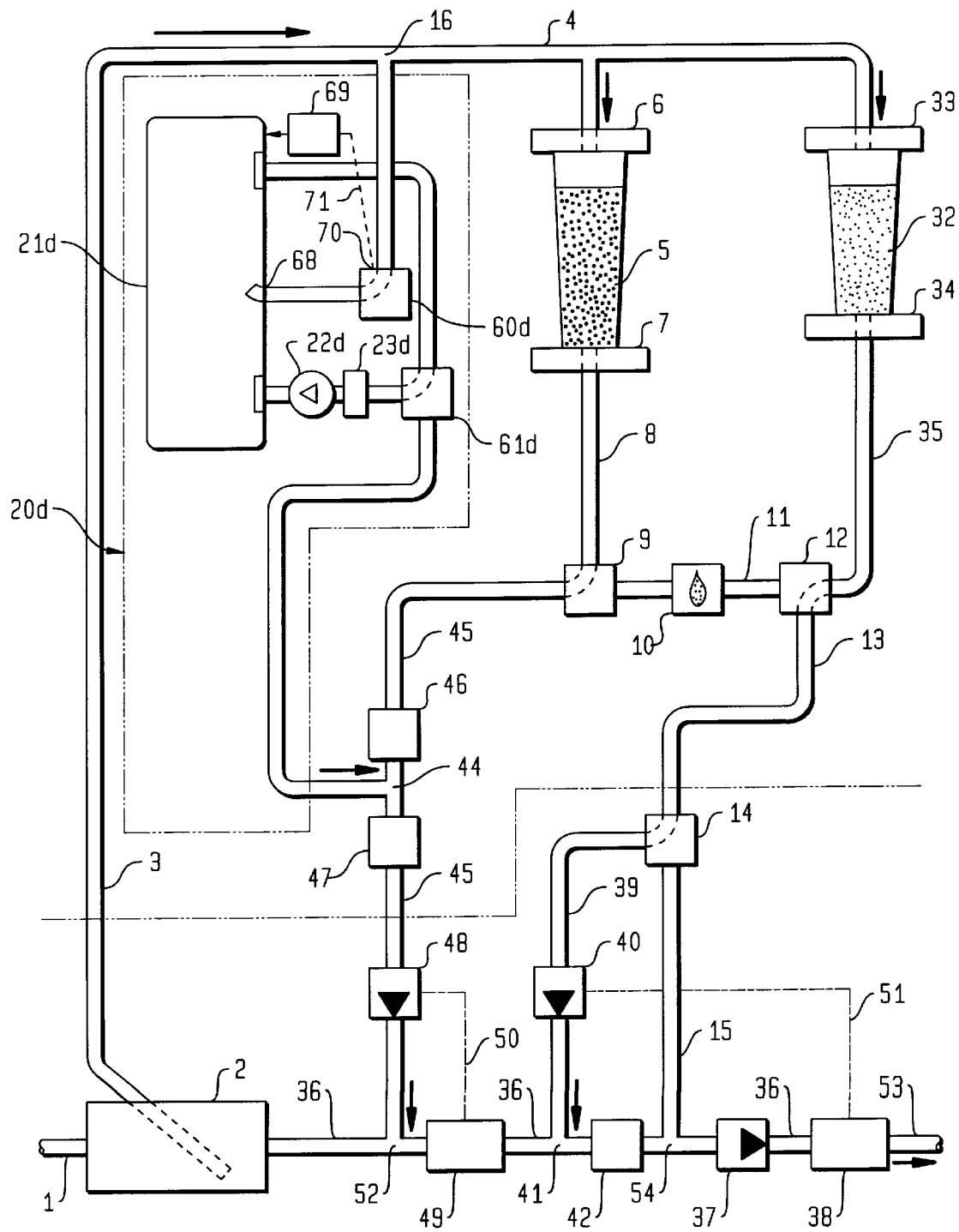
FIG. 9 is a schematic representation of yet a further modified embodiment of the system in accordance with the present invention.

A further embodiment of the present invention is illustrated in FIG. 9. This embodiment also has similar reference numerals to that previously discussed hereinabove except that reference letter "d" is utilized. In this embodiment, bag 21d has a separate connector 68 through which water is supplied thereto. In all other respects, the embodiment shown in FIG. 9 is similar to the embodiment shown in FIGS. 6 and 8. The connector 68 is preferably a quick-release connector. It is also preferable to arrange the inlet extending through connector 68 in such a manner so that a vortex is formed inside the bag 21d upon flowing of water therein. It is preferable in this embodiment, for the quick-release connector 68 to include an angled portion which directs the incoming water tangentially to the bag so that advantageous dissolution of the solid substances therein is obtained.

The embodiment shown in FIG. 9 also includes a level indicator 69 which is adapted to detect when a sufficient amount of water has been introduced into the bag 21d. The level sensor 69 can be adapted to operate an inlet valve 70 via communication link 71 (shown as a dotted line) to selectively permit water to enter into the bag 21d. In this embodiment, water can be introduced into the bag 21d by gravity or other suitable means. The use of level sensor 69 is advantageous when the manner of obtaining the desired level of conductivity in accordance with FIG. 7 is utilized. This will permit a determination to be made as to the exact quantity of water needed to be introduced into the bag 21d when used in conjunction with a conductivity meter activated after initial mixing of the water and the solid substances within the bag 21d.

Figure 10:
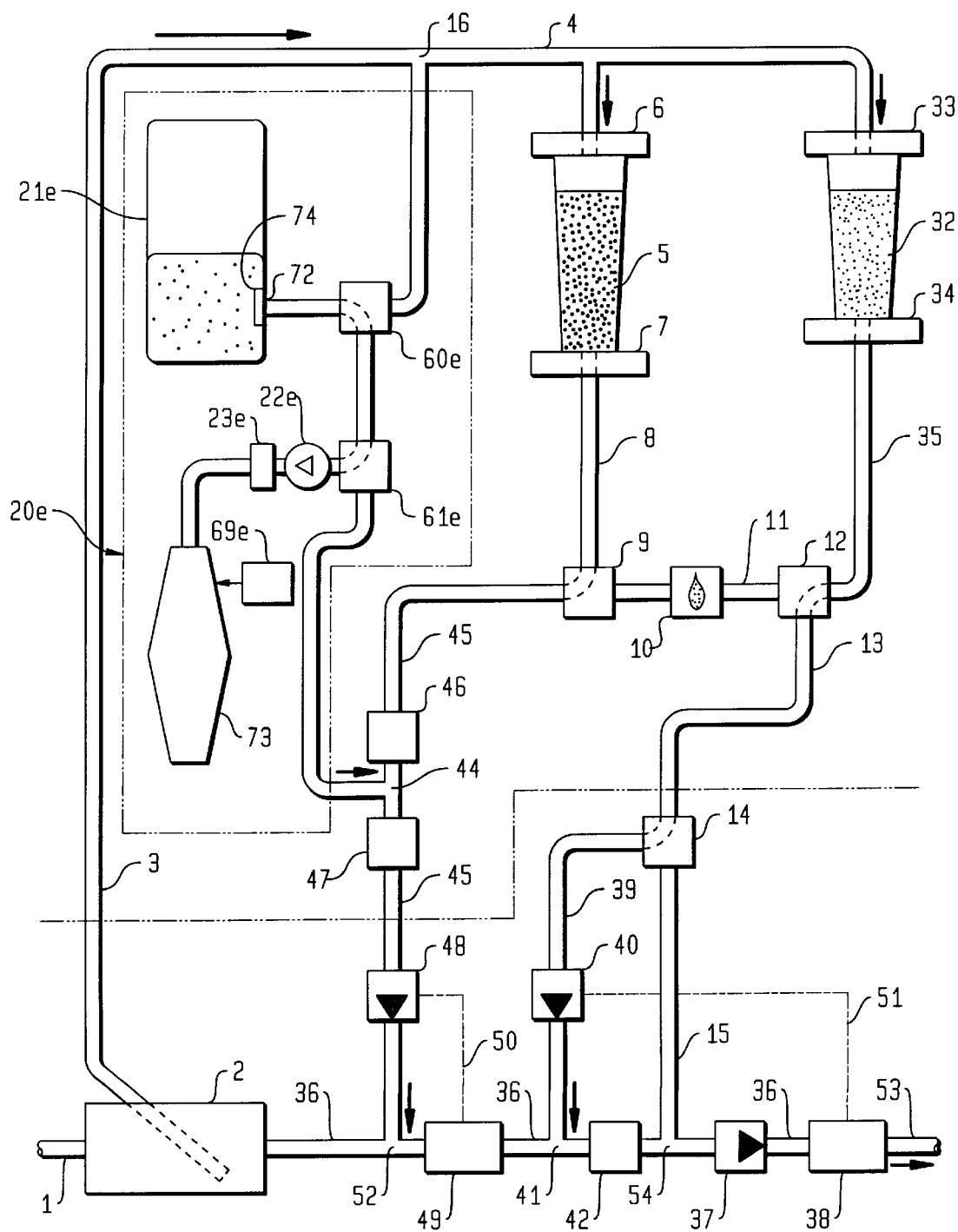
FIG. 10 is a schematic representation of still another modified embodiment of the system in accordance with the present invention.

A final embodiment of the present invention is illustrated in FIG. 10. In this embodiment, similar reference numerals are again used when appropriate with the exception that reference letter "e" is utilized. According to this embodiment, the bag 21e has a single lower connector 72. The inlet valve 60e permits water to be introduced to a conduit which flows through the lower connector 72 and into the bag 21e. The inlet value 60e may be actuated to a lower portion of the conduit which leads to outlet valve 61e. When in a selected position, the outlet valve 61e permits communication with pump 22e, conductivity meter 23e and a second bag 73. The second bag 73 may comprise a flexible material, or may include a rigid container.

During operation of the recirculation circuit 20e shown in the embodiment of FIG. 10, the inlet valve 60e is placed in its second position at which time water is introduced into the container 73 via pump 22e. When a predetermined amount of water has been introduced into container 73, as measured by metering pump 22e or by level indicator 69e, inlet valve 60e is then placed into the position shown in FIG. 10 and water is no longer permitted to flow into the container. The water in container 73 is then removed via pump 22e and forced to flow into bag 21e through the conduit which leads through connector 72, thus exposing the solid substances within the bag 21e to the water. The pump 22e is then reversed and the partially prepared concentrate solution, including water and some of the solid substances which have been dissolved, are then withdrawn through the connector 72 and back into container 73. This procedure is continuously repeated until it is determined that all of the solid substances in bag 21e are completely dissolved. When this state has been achieved, the final concentrate solution is then ready to be transported into container 73. Outlet valve 61e may then be placed into its second position wherein the final concentrate solution may be delivered to mixing point 44.

Optionally, the conductivity meter 23e and the metering pump 22e may be placed between the connector 72 and the valve 60e.

The bag 21A is sized to enclose all of the prepared final concentrate solution, which will then be selectively delivered to the mixing point 44.

Container 73 may be made of a flexible material whereby no air is admitted into the system. Alternatively, container 73 has a rigid construction and is open to the atmosphere. In all of the embodiments discussed hereinabove, it should be appreciated that bags 21 a–e may be provided with a filter, such as filter 74 shown in FIG. 10 which is adapted to prevent solid particles above a predetermined size to flow into and/or out of the bag 21 a–e in an undissolved condition.

When desired, acid can be added into the recirculation circuit in the same way as described with regard to FIG. 6. Alternatively, acid may be placed into the system by introducing it into the slurry as discussed with regard to example 1 hereinabove. Further, if desired, certain dry acids in powder form may be utilized.

Various modifications of the embodiments of the present invention may be utilized while staying within the scope set forth in the claims. In this regard, when the embodiment shown in FIG. 5A is utilized, the bag 21a may be provided with a separate unit for water, similar to the unit shown in FIG. 9. The concentrate solution prepared by recirculation according to the present invention can be prepared batchwise at the initiation of a medical treatment. It should be appreciated that the time for dissolving the solid or powdered substances from a dry state is usually less than about five minutes.

In alternate embodiments, several bags having different compositions can be prepared in advance to enable the operator to exchange the composition of salts during a medical treatment which can last for more than four hours. Such exchange of compositions can be exclusion of potassium from the composition or otherwise profiling the composition of electrolytes. When it is determined that the composition should be changed, the current bag 21 a–e, included in the dialysis equipment, is disconnected by using the quick-release connectors and a new bag, including already dissolved substances, may be easily connected in its place.

Another way to perform the same operation is to interrupt a medical treatment for a short time sufficient for removing the original bag 21 a–e, and replace it with a new bag retaining dry powder therein. Water may then be introduced into the bag and the concentrate solution can be recirculated until a final concentrate solution is obtained, at which time the medical treatment may be restarted. Short interruptions, such as interruptions of five minutes or less, would be acceptable under certain conditions.

It should be appreciated that the same principles described with regard to FIG. 6–10 for integral bath preparation of the concentrate solution in bags 21 a–e within the medical treatment device, can also be utilized in separate bath concentrate solution preparation machines, such as the device disclosed in FIG. 5A and 5B, whereupon the concentrate solution thus formed is removed from the second machine for subsequent use at a dialysis machine, or similar device, possibly after stopping a short time, such as a few hours.

Naturally, the invention is not limited simply to the embodiment described above, but may be varied within the scope of the following claims. The parts included in the system may thus be varied within wide limits with regard to their form as well as their function.

What is claimed is:

1. An apparatus for preparing a concentrate solution which may be used as a medical solution, comprising: a liquid supply for supplying a predetermined amount of liquid; a mixing container adapted to receive said liquid; a plurality of vessels containing powder therein to be partially dissolved in said liquid; a flow path including at least one conduit for the flow of liquid from said mixing container through a selected one of said vessels and for the return flow of the liquid and dissolved powder therein to said mixing container; a valve assembly for selectively directing the flow of said liquid and said dissolved powder to one of said plurality of vessels until a predetermined amount of said powder has been dissolved, whereupon said valve assembly will direct the flow of said liquid and dissolved powder to a further one of said vessels as said liquid and dissolved powder flow through said flow path until a concentrate solution having a desired concentration is obtained.

2. The apparatus of claim 1 further comprising a pump arranged within said flow path for facilitating recirculation of the liquid and dissolved powder therein.

3. The apparatus of claim 1 further comprising concentration determination means arranged within said flow path for determining the concentration of the liquid and dissolved powder and for regulating the concentration thereof.

4. The apparatus of claim 3 wherein said concentration determination means includes a conductivity measuring device for measuring the conductivity of the liquid and dissolved powder whereby recirculation of the liquid and dissolved powder in said recirculation means can be controlled thereby.

5. The apparatus of claim 4 wherein said valve assembly is operatively associated with said conductivity measuring device whereby said valve assembly is selectively actuated direct to flow of the liquid and dissolved powder recirculating in said recirculation flow path to a selected one of said plurality of vessels.

6. The apparatus of claim 1 further comprising a heating device for heating the liquid provided from said liquid supply.

7. The apparatus of claim 1 further comprising a level detector arranged in said flow path for detecting when a sufficient amount of liquid has been supplied.

8. The apparatus of claim 1 wherein said plurality of vessels comprises three vessels, each of said vessels containing different powders including salt.

9. An apparatus for preparing a concentrate solution which may be used as a medical solution, comprising: a mixing container adapted to retain a predetermined amount of liquid; a plurality of vessels containing powder therein to be dissolved in said liquid; flow path including at least one conduit for the flow of liquid from said mixing container through a selected one of said vessels and for the return flow of the liquid and dissolved powder therein to said mixing container; a valve assembly for selectively directing the flow of said liquid and said dissolved power to one of said plurality of vessels until a predetermined amount of powder has been dissolved, whereupon said valve assembly will direct the flow of said liquid and dissolved powder to a further one of said vessels as said liquid and dissolved powder flow through said flow path until the concentrate solution having a desired concentration is obtained.

10. The apparatus of claim 9 further comprising a pump arranged within said flow path for facilitating recirculation of the liquid and dissolved powder therein.

11. The apparatus of claim 9 further comprising concentration determination means arranged within said flow path for determining the concentration of the liquid and dissolved powder and for regulating the concentration thereof.

12. The apparatus of claim 11 wherein said concentration determination means includes a conductivity measuring device for measuring the conductivity of the liquid and dissolved powder whereby recirculation of the liquid and dissolved powder in said recirculation means can be controlled thereby.

13. The apparatus of claim 12 wherein said valve assembly is operatively associated with said conductivity measuring device whereby said valve assembly is selectively actuated to direct the flow of the liquid and dissolved powder recirculating in said flow path to a selected one of said plurality of vessels.

14. The apparatus of claim 9 further comprising a heating device for heating liquid provided to said flow path.

15. The apparatus of claim 9 further comprising a level detector arranged in said flow path for detecting when a sufficient amount of liquid has been supplied.

16. The apparatus of claim 9 wherein said plurality of vessels comprises three vessels, each of said vessels containing different powders including salt.

17. A method of preparing a concentrate solution which may be used as a medical solution from an apparatus including a mixing container and a plurality of vessels each having a powder therein, said method comprising the steps of:

supplying a predetermined amount of water to the mixing container;

selectively transporting the water from said mixing container through a first one of said plurality of vessels so that a predetermined amount of the powder in said selected vessel is dissolved in the water;

terminating said flow of water through said first one of said vessels when a predetermined amount of said powder has been dissolved and the concentration of said powder in said water has reached a predetermined concentration whereupon a partially prepared concentrate solution is obtained;

selectively transporting said partially prepared concentrate solution from said mixing container to a further one of said plurality of vessels so that a predetermined amount of powder in said further selected vessel is dissolved in said partially prepared concentrate solution;

terminating the flow of the partially prepared concentrate solution through said further selected vessel when the concentration of said partially prepared concentrate solution has reached a predetermined concentration;

repeating the steps of selectively transporting said partially prepared concentrate solution from said mixing container to a further one of said vessels and dissolving a predetermined amount of powder therein until a final desired concentrate solution is obtained; and transporting said final desired concentrate solution to a desired site.

18. The method of claim 17, further comprising:

measuring the concentration of said powder in said partially prepared concentrate solution and terminating the flow of said partially prepared concentrate solution through a selected one of said vessels when a desired concentration has been obtained.

19. The method of claim 18, wherein said measuring step comprises measuring the conductivity of the concentrate solution.

20. The method of claim 17, wherein said step of transporting water or partially prepared concentrate solution comprises pumping said water or partially prepared solution.

21. The method of claim 17, further comprising the step of heating said water.

22. The method of claim 21 wherein said water is heated to about 37° C.

23. The method of claim 17, wherein said plurality of vessels comprises three vessels, and said powder in said vessels includes three different salts, said steps of dissolving powder comprising dissolving the salts.

24. The method of claim 17, further comprising the step of diluting or dissolving a liquid-based concentrate solution retained in a further vessel within said partially prepared concentrate solution to obtain the final concentrate solution.

25. An apparatus for preparing a concentrate solution which may be used as a medical solution comprising:

a container;

water supply means for supplying a predetermined amount of water to said container;

a plurality of vessels, each containing an in water dissolvable solid substance;

a flow path including at least one conduit for the flow of liquid between said container and said plurality of vessels, flow means for transporting said predetermined amount of water within said flow path and said container and a first of said vessels, for at least partially dissolving the solid substance of said first vessel until a partially prepared concentrate solution having a predetermined concentration is obtained, said flow means including valve means for selectively connecting said container to a further of said plurality of vessels whereby each vessel is successively incorporated one by one into the flow path so that said partially prepared solution within said flow path will at least partially dissolve the solid substance of each of said vessels until a final concentrate solution having a predetermined concentration is obtained; and concentration determination means arranged within said flow path for determining the concentration level of the partially prepared solution within said flow path, said flow means further comprising control means for terminating the flow of solution through a selected one of said vessels, which is connected to said flow path, when a predetermined concentration level has been obtained as determined by said concentration determination means, said final concentrate solution being transported through said flow path to a desired site.

26. The apparatus of claim 25 wherein said concentration determination means comprises a conductivity meter for determining the conductivity and thus the concentration level of said partially prepared solution.

27. The apparatus of claim 25 wherein said flow means comprises pump means for pumping the partially prepared solution within the flow path.

28. The apparatus of claim 27 wherein said pump means further comprises metering means for metering the concentrate solution to an outlet conduit to withdraw said concentrate solution for use as a medical solution.

29. The apparatus of claim 28 further comprising an outlet valve for connecting said container to said outlet conduit.

30. The apparatus of claim 25 further comprising heating means for heating said supplied water.

31. The apparatus of claim 25 wherein said water supply means comprises valve means for terminating said supply of water when the predetermined amount of water has been supplied.

32. The apparatus of claim 25 wherein said plurality of vessels contains an excess of solid substances, so that said concentrate solution can be prepared with the content of said plurality of vessels.

33. The apparatus of claim 25 wherein said plurality of vessels comprises three vessels each having a different salt therein.

34. The apparatus of claim 25 wherein each of said plurality of vessels is a cartridge.

35. The apparatus of claim 25 further comprising a further vessel connected in parallel with said plurality of vessels and containing a liquid-based concentrate solution intended to be included in the concentrate solution.

36. The apparatus of claim 35 wherein said further vessel is connected to said water supply means for mixing said liquid-based concentrate solution with water and supplying said mixture to said container.

37. The apparatus of claim 25 further comprising a level indicator for terminating the supply of water when the predetermined amount of water has been supplied.

38. The apparatus of claim 25 further comprising:

a secondary vessel containing an in water dissolvable solid substance;

secondary water supply means for supplying water to said secondary vessel for dissolving said solid substance and forming a secondary concentrate solution; and mixing means for mixing said secondary concentrate solution with said concentrate solution withdrawn from said flow means for forming said concentrate solution.

39. The apparatus of claim 38 further comprising:

a tertiary vessel containing an in water dissolvable solid substance;

tertiary water supply means for supplying water to said tertiary vessel for dissolving said solid substance and forming a tertiary concentrate solution;

mixing means for mixing said tertiary concentrate solution with said concentrate solution withdrawn from said flow means, possibly mixed with said secondary concentrate solution for forming said concentrate solution.

* * * * *

UNITED STATES PATENT AND TRADEMARK OFFICE
CERTIFICATE OF CORRECTION

PATENT NO. : 6,149,294
DATED : November 21, 2000
INVENTOR(S) : Jönsson et al.

It is certified that error appears in the above-identified patent and that said Letters Patent is hereby corrected as shown below:

On title page,

In the Attorney, Agent, or Firm Section, "Littenburg" should read -- Littenberg --.

Signed and Sealed this

Twenty-ninth Day of May, 2001

*Attest:*

NICHOLAS P. GODICI

*Attesting Officer*     *Acting Director of the United States Patent and Trademark Office*

UNITED STATES PATENT AND TRADEMARK OFFICE
CERTIFICATE OF CORRECTION

PATENT NO.    : 6,149,294
DATED         : November 21, 2000
INVENTOR(S)   : Jönsson et al.

It is certified that error appears in the above-identified patent and that said Letters Patent is hereby corrected as shown below:

<u>Title page,</u>
Item [74], *Attorney, Agent or Firm*, "Littenburg" should read -- Littenberg --.

Signed and Sealed this

Tenth Day of May, 2005

JON W. DUDAS
*Director of the United States Patent and Trademark Office*